US009664666B2

(12) United States Patent
Lavenson et al.

(10) Patent No.: US 9,664,666 B2
(45) Date of Patent: May 30, 2017

(54) APPARATUS AND METHODS FOR QUALIFYING COMPOSITIONS

(71) Applicants: David Michael Lavenson, Houston, TX (US); Ramachandran Venkatesan, Katy, TX (US); Lee David Rhyne, Cypress, TX (US); Laurence Ann Washington, Houston, TX (US)

(72) Inventors: David Michael Lavenson, Houston, TX (US); Ramachandran Venkatesan, Katy, TX (US); Lee David Rhyne, Cypress, TX (US); Laurence Ann Washington, Houston, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 458 days.

(21) Appl. No.: 14/533,202

(22) Filed: Nov. 5, 2014

(65) Prior Publication Data

US 2015/0127315 A1 May 7, 2015

Related U.S. Application Data

(60) Provisional application No. 61/900,591, filed on Nov. 6, 2013.

(51) Int. Cl.
*G06G 7/48* (2006.01)
*G01N 33/28* (2006.01)
(Continued)

(52) U.S. Cl.
CPC ......... *G01N 33/2835* (2013.01); *C09K 8/524* (2013.01); *C10L 1/14* (2013.01); *E21B 37/06* (2013.01)

(58) Field of Classification Search
CPC .... C09K 8/524; C09K 8/588; G01N 33/2823; C10L 1/14; C10L 1/2364; E21B 37/06
See application file for complete search history.

(56) References Cited

U.S. PATENT DOCUMENTS 3,840,352 A * 10/1974 Scheffel ............... C10L 1/14
  44/393
4,045,360 A * 8/1977 Fischer ................. C09K 8/524
  166/304

(Continued)

OTHER PUBLICATIONS

Johnson, et al. Studies of Paraffin Wax Deposition on Coated and Non-Coated Steel Surfaces, Proceedings of International Conference on Heat exchanger Fouling and Cleaning—2011, Jun. 5-10, 2011, Crete Island, Greece, 8 pages.

(Continued)

*Primary Examiner* — Kandasamy Thangavelu
(74) *Attorney, Agent, or Firm* — Karen R. DiDomenicis; Andrews Kurth LLP

(57) ABSTRACT

A test apparatus for qualifying compositions used to reduce scale deposition in fluid, e.g., wax deposition in crude oil, is disclosed. The test apparatus includes a first reservoir capable of holding a first fluid, and a second rotatable reservoir disposed within the first reservoir, the second reservoir capable of holding a second fluid. The apparatus includes a fluid inlet through which the second fluid enters the second reservoir, and a fluid outlet through which the second fluid exits the second reservoir, wherein a bottom surface of the second rotatable reservoir is configured to be at least partially submerged in the first fluid so that precipitate from the first fluid can be deposited thereon.

21 Claims, 2 Drawing Sheets

(51) Int. Cl.
*C09K 8/524* (2006.01)
*E21B 37/06* (2006.01)
*C10L 1/14* (2006.01)

(56) References Cited

U.S. PATENT DOCUMENTS

| | | | | |
|---|---|---|---|---|
| 2001/0056164 A1* | 12/2001 | Duncum | ................ | C09K 8/524 526/319 |
| 2003/0071988 A1* | 4/2003 | Smith | .................... | E21B 37/06 356/128 |
| 2008/0190180 A1* | 8/2008 | Zougari | ............. | G01N 33/2823 73/61.62 |
| 2009/0005490 A1* | 1/2009 | Forsyth | ................. | C09K 8/588 524/475 |
| 2009/0233817 A1* | 9/2009 | Kriegel | ................ | C10L 1/2364 507/90 |

OTHER PUBLICATIONS

Venkatesan et al., Study of wax inhibition in different geometries, OTC 23624, Offshore Technology Conference , 2012, 5 pages.
Elton B. Hunt, Jr. , Petroleum Transactions, Laboratory Study of Paraffin Deposition, SPE 279, Journal of Petroleum Technology, Nov. 1962, pp. 1259-1269.

* cited by examiner

APPARATUS AND METHODS FOR QUALIFYING COMPOSITIONS

CROSS-REFERENCE TO RELATED APPLICATIONS

This application claims benefit under 35 USC 119 of U.S. Provisional Patent Application No. 61/900,591 with a filing date of Nov. 6, 2013, incorporated herein by reference in its entirety.

TECHNICAL FIELD

The invention relates generally relate to apparatuses for qualifying chemical compositions for reducing scale deposition such as wax deposition.

BACKGROUND

Deposition of scale or waxes causing fouling of pipelines is a costly and common problem in the oil industry. Compositions such as wax inhibitors are sometimes used to reduce the rate of wax deposition in pipelines. The efficiency of the inhibitors depends on several factors such as the right chemistry, injection or introduction at the correct location, targeting the right operating conditions and testing appropriately. Bench or lab-scale testing of wax deposition is useful for screening and measuring the efficiency of various inhibitor chemicals. It is known however that bench top tests such as cold finger tests, while useful to qualitatively gauge chemical performance, may not be useful to quantitatively predict the performance of a chemical under field operating conditions. This is because the operating parameters such as the temperature difference, heat flux, and shear rates experienced in the field cannot be reproduced in such bench top devices simultaneously. Furthermore, electrochemical cells in the prior art are based on laminar flow and well defined analytical solutions for the flow field, concentration gradients, etc.

There is a need for a testing apparatus for qualifying inhibitor compositions used to reduce scale/wax deposition in pipelines, capable of quantitatively predicting the performance of various inhibitors under more realistic field operating conditions. There is also need for a testing apparatus for electrochemical cells that uses a turbulent flow field.

SUMMARY

In one aspect, embodiments disclosed herein relate to a testing apparatus for qualifying chemical inhibitors used to reduce wax deposition, the apparatus including a first reservoir capable of holding a first fluid, a second rotatable reservoir disposed within the first reservoir, the second reservoir capable of holding a second fluid, wherein a height of the first reservoir is less than three times a width of the second reservoir, and wherein a width of the first reservoir is less than two times a width of the second reservoir, and a fluid inlet through which the second fluid enters the second reservoir, and a fluid outlet through which the second fluid exits the second reservoir, wherein a bottom surface of the second rotatable reservoir is configured to be at least partially submerged in the first fluid so that wax precipitate from the first fluid is deposited thereon.

In other aspects, embodiments disclosed here relate to a method for qualifying chemical inhibitors used to reduce wax deposition, the method including providing a first reservoir capable of holding a first fluid, and a second reservoir capable of holding a second fluid, wherein a height of the first reservoir is less than three times a width of the second reservoir, and wherein a width of the first reservoir is less than two times a width of the second reservoir, contacting a bottommost surface of the second reservoir with the first fluid in the first reservoir, adjusting a temperature $T_2$ of the second fluid to be less than a temperature $T_1$ of the first fluid, adding one or more chemical inhibitors to the first fluid, rotating the second reservoir at a given speed, and collecting wax precipitate from the first fluid deposited on a bottommost surface of the second reservoir.

BRIEF DESCRIPTION OF THE DRAWINGS

The invention is illustrated in the accompanying drawings wherein.

DETAILED DESCRIPTION

Figure 1:
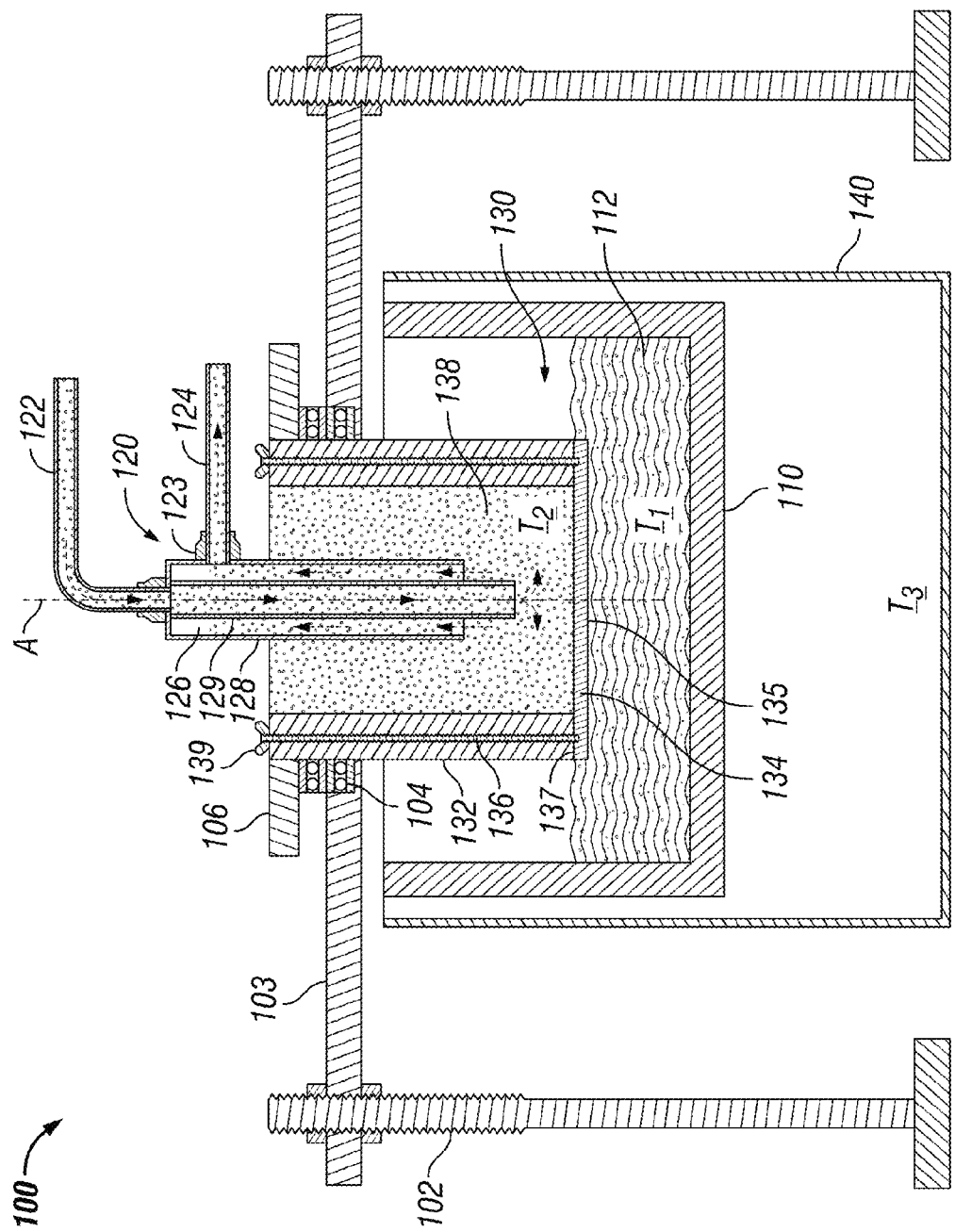
FIG. 1 illustrates a cross-section view of an embodiment of a test apparatus for qualifying chemical inhibitors used to reduce wax deposition.

The aspects, features, and advantages of the invention mentioned above are described in more detail by reference to the drawings, wherein like reference numerals represent like elements.

A testing apparatus for qualifying compositions used to reduce scale/deposition in pipelines is disclosed. The apparatus can simulate both laminar and turbulent flow in pipelines. The apparatus includes a fixed first reservoir capable of holding a first fluid at a temperature T1, and a rotatable second reservoir capable of holding a second fluid at a temperature T2. The first reservoir may be filled with the first fluid to any level, although typically the first reservoir will be not completely filled. Likewise, the second reservoir may be filled with the second fluid to any level. The first fluid in the first reservoir is oil, such as crude oil found in pipelines. Various chemical inhibitors to be tested may be mixed into the oil. The second fluid is a coolant, e.g., heat exchange fluids, water, glycol, etc., with the choice depends on the operating temperature for testing. The rotatable second reservoir is smaller, e.g., having a smaller dimension, than the first reservoir such that the second reservoir is inserted into the first reservoir so that a bottommost surface of the second reservoir is partially submerged in the first fluid. The bottommost surface of the second reservoir serves as a "cold" wax deposition surface, which stated otherwise, means wax precipitate from the first fluid, or oil, is deposited onto the bottommost surface of the second reservoir during testing. The first and second reservoirs may be made out of stainless steel or other metal, materials, with a bottom and wall thickness ranging from 5-20 mm in one embodiment.

The testing apparatus is used for qualifying compositions such as chemical inhibitors used to reduce deposition in pipelines, e.g., wax, scale, asphaltenes, etc. In one embodiment of a test to qualify chemical inhibitors, the first reservoir is filled with oil or other fluid to be tested ("first fluid"). Chemical inhibitors to be tested are also added to the first fluid. The temperature in the first reservoir is raised to a temperature T1 and maintained at or about T1. In one embodiment, T1 is the wax appearance temperature (WAT), ranging from room temperature to about 60° C. WAT is generally the temperature at which, on a cooling cycle, crude oil first precipitates solid wax.

The second reservoir is inserted within the first reservoir with the bottommost surface of the second reservoir submerged in the first fluid (e.g., oil with chemical inhibitors) in the first reservoir. A second fluid, e.g., coolant, at or below temperature T2 is pumped into the second reservoir for the walls and bottom surface of the second reservoir to reach a temperature substantially close to or the same as T2. During testing, the second reservoir is rotated at a given speed, while maintaining temperature T2 at less than first fluid temperature T1 and Wax Appearance Temperature. During testing, e.g., for a period of at least 15 minutes, wax precipitates from the oil in the first reservoir and is deposited on the bottommost surface of the second reservoir. After a certain amount of time, e.g., for at least 20 minutes, the rotation of the second reservoir can be stopped and the second reservoir can be removed from the first reservoir. The bottom disk of the second reservoir can be removed to observe and analyze wax deposition. The effectiveness of the chemical inhibitors present in the first fluid during testing may be determined based on wax deposition on the bottom surface. Because the bottommost surface is a solid disk, as the bottom surface rotates, variable shear stresses are imparted on the fluid allowing the testing of the effect of wax inhibitors at different shear stress levels. Furthermore, the rotation speed can be adjusted such to achieve laminar and turbulent flow during deposition. Simulating turbulent flow is particularly useful in mimicking pipe flow in operations.

In one embodiment, the testing apparatus includes a first temperature control device for adjusting or maintaining a temperature of the first fluid at or about temperature T1. In one embodiment, the first temperature control device may include a heat transfer fluid (e.g., a temperature controlled bath) which contacts the first reservoir. The heat transfer fluid, or third fluid, may be at or above a temperature T3, which is greater than T2. As another example, the temperature T1 of the first fluid in the first reservoir may be adjusted or maintained by submerging all or a portion of the first reservoir in a heat transfer fluid or temperature controlled bath, the temperature controlled bath containing the third fluid at a temperature T3 (which is above the WAT), e.g., from 25 to 70° C. Other devices for maintaining the first fluid at or above temperature T1 may also be used, including electrical heating elements, electrical tapes for wrapping around the first reservoir.

In one embodiment, the testing apparatus may further include a second temperature control device for adjusting or maintaining a temperature of the second fluid (coolant) at or below a temperature T2, e.g., in a range from 5-30° C. In one embodiment, the second temperature control device comprises chilling coils inserted into or wrapped around the second reservoir. Alternatively, the second temperature control device may include chilling coils in a separate storage tank or container holding the second fluid.

In one embodiment, temperature T2 of the second fluid is less than the temperature T1 of the first fluid. In one embodiment, the testing apparatus further includes a coolant fixture for delivering to and removing the second fluid, or coolant, from the second reservoir. The coolant fixture includes a fluid inlet and fluid outlet in fluid communication with a separate fluid storage tank. The coolant may enter and exit the second reservoir at varying flow rates depending upon various cooling requirements. Coolant may be stored separately in a coolant storage tank.

The first and second reservoirs may have cylindrical or elliptical cross-sections. Alternatively, the first and second reservoirs may have polygonal cross-sections. Sizing of the first and second reservoirs may vary according to any number of testing requirements. The first and reservoirs can be constructed out of the same or different materials, carbon steel, stainless steel, alloys, polymeric materials, and the like. The reservoirs may have the same or different wall thicknesses and bottom thicknesses, ranging in one embodiment from 2 to 30 mm.

The depth of the first reservoir varies depending upon a width or diameter of the second reservoir bottom surface. In one embodiment, the first reservoir may have a depth that is no more than three times a width or diameter of the bottommost surface of the second reservoir. In another embodiment, the first reservoir may have a depth that is no more than two times a width or diameter of the bottommost surface of the second reservoir. In yet another embodiment, the first reservoir may have a depth that is no more than five times a width or diameter of the bottommost surface of the second reservoir.

In addition, the first reservoir width or diameter may vary depending, in some instances, upon the second reservoir bottom surface dimension, e.g., width or diameter. In one embodiment, the first reservoir has a dimension of less one half of a similar dimension (e.g., a width or diameter) of the second reservoir bottom surface. In another embodiment, the first reservoir diameter has a dimension of less than $\frac{1}{3}$ of a similar dimension of the second reservoir bottom surface. In yet another embodiment, the first reservoir has a width or diameter of at least less than 1.5 times the second reservoir bottom surface width or diameter.

The second reservoir may be arranged in a substantially vertical manner having a vertical central axis. The second reservoir may include a substantially flat bottommost surface, e.g., a disk, which is removable and interchangeable in one embodiment. For example, the bottommost removable surface may be either a metal and non-metal material. And the bottommost surface may be attached to the second reservoir in a manner so that there are no protrusions into the first fluid on the bottommost surface when the bottommost surface is submerged in the first, which might create disturbances in a flow field of the first fluid. For example, the bottommost surface may be a substantially flat plate having a cross-section corresponding with a cross-section of the second reservoir. The plate may have a circular, elliptical, polygonal or other corresponding cross-section.

The second reservoir may be supported on a fixed structure while it is disposed within the first reservoir. In one embodiment, the second reservoir includes a flanged surface that rests on a portion of the fixed structure so that the second reservoir is suspended within the first reservoir. In another embodiment, the second reservoir may be supported on a plurality of bearings allowing the second reservoir to rotate. The second reservoir may be coupled to a motor by way of an elastic belt, with the motor operating to rotate the second reservoir during testing. The motor may be operable at a number of variable speeds for simulating different testing conditions, such as introducing laminar or turbulent flow conditions.

The dimensions of the reservoirs (of the test apparatus) can be determined by Computational Fluid Dynamics (CFD) simulations of the flow field. CFD models can help fine-tune the dimensions to provide an optimal geometry for the specific tests being performed. With the use of the apparatus/method, many effects can be optimized with CFD models to allow the data to be appropriately scaled to field conditions.

When fluids (e.g., hydrocarbons such as crude oils) traverse through a pipe, they exert force on the walls of the pipe. In operations, fluids and their admixtures are subjected to various "shear rates." The shear rates they are subject to are a function of the geometry across which the fluids flow, and the local velocity at which they travel. Data from rheological tests including shear stress response of fluids at various shear rates can be used as input to the CFD models. Besides test reservoir dimensions, the CFD simulations can also be used to indicate the appropriate rotating cylinder size and shear rates at various RPMs, including the functional relationship between these quantities in the laminar and turbulent regimes. Output of the CFD simulations can be used to effectively determine size the test apparatus and determine the rotation rates given the rheological properties of the fluids being tested.

In one embodiment of a test apparatus with the temperature control features of the test fluid (in the first reservoir), the cold deposition surface (bottom surface of the second reservoir), and the rotational speed of the second reservoir, provides a shear field that varies along the cold surface. With the use of a rotating cylinder, the shear field radially across the spinning cylinder surface can be manipulated by the rotation rate, which is substantially free of vibrational noise from the motor. In yet another embodiment, the deposition results are used to scale to pipe-flow conditions. In another embodiment, a removable/interchangeable disk is used as the (rotational) bottom of the second reservoir, allowing easy cleaning as well as the implementation of different surface materials for the disk for test simulations.

In one embodiment, the test apparatus is an assembly with a plurality of test cells, with each test cell having its own first and second reservoirs for the testing of different compositions, e.g., wax inhibitors, at different temperature T2's. In one embodiment, the test cells are linearly positioned with a single motor for testing at identical speed. In another embodiment, each test cell is provided with its own motor for the test cells to be tested under different conditions at the same time, e.g., laminar or turbulent.

In another embodiment, the test apparatus is an assembly of a single large reservoir (functioning as the first reservoir) and a plurality of second reservoirs for the testing of different compositions. The assembly is configured with a retaining frame for securing the plurality of second reservoirs in suspension in the first reservoir. The retaining frame is further configured for holding a plurality of rotating shafts, one for each second reservoir, with the shaft speeds can be adjusted for testing in either laminar or turbulent flow mode for each of the second reservoir.

The test apparatus can be used to qualify/evaluate compositions such as wax inhibitors. The apparatus can also be used to evaluate temperature-driven deposition of other hydrocarbons such as with known shear field, e.g., asphaltenes, scales. In yet another embodiment, the apparatus can be used for scale deposition testing using temperature sweep with known shear field and/or known turbulence levels in sample. In another embodiment, it is employed for crystal growth experiments with known shear and/or turbulence. Lastly, the apparatus can be used for determination of boundary layer characteristics in varying turbulence levels through using optical or electrochemical tracer techniques.

References will be made to the figures that illustrate the prior art and different embodiments of the invention. The figures include examples of how a person of ordinary skill in the art can make and use the claimed invention. It is described here to meet the enablement and best mode requirements of the patent statute without imposing limitations that are not recited in the claims. The various parts of the illustrated apparatus, as shown, described and claimed, may be of either original and/or retrofitted construction as required to accomplish any particular implementation of the invention, and all or part of each embodiment can be used in combination with all or part of any one or more of the others.

FIG. 1 illustrates a cross-section view of a testing apparatus 100 for qualifying chemical inhibitors used to reduce wax deposition in accordance with one or more embodiments. The apparatus 100 includes a first reservoir 110 containing a first fluid 112 at temperature T1. As shown, the first reservoir 110 may be any fluid containing device having an open top. In one embodiment, the first fluid 112 contained in the first reservoir 110 may be oil (e.g., crude oil), or any other type of hydrocarbon fluid for testing. The first fluid 112 may be temperature controlled by submerging all or a portion of the first reservoir 110 in a temperature controlled bath 140, the temperature controlled bath 140 containing a separate fluid at or above a temperature T3.

The testing apparatus 100 further includes a rotatable second reservoir 130 containing a second fluid 138 at a temperature T2. A portion of the second reservoir 130 may be submerged in the first fluid 112 of the first reservoir 110. The second reservoir 130 includes a hollow body 132, which in certain embodiments may be a cylinder 132, arranged in a substantially vertical manner and having a vertical central axis A, and a substantially flat bottom plate, which in certain embodiments may be a circular disk 134, attached at a bottommost end of the hollow cylinder 132. The bottom disk 134 is attached at a lower end of the hollow cylinder 132, thereby enclosing a lower end of the cylinder 132 and forming the second reservoir 130. An O-ring (not shown) or other sealing device may be disposed between at upper surface 137 of the bottom disk 134 and the hollow cylinder 132 to seal the bottom disk 134 to the cylinder 132 and prevent leakage of the second fluid 138 into the first reservoir 110. A bottom surface 135 of the bottom disk 134 is submerged in the first fluid 112 in the first reservoir 110. During testing, wax is deposited on the bottom surface 135 of the bottom disk 134. The bottom surface 135 of the bottom disk 134 may be substantially flat and without protrusions, which substantially prevents disturbances to the flow field during wax deposition.

The bottom disk 134 may be attached to a bottommost end of the hollow cylinder 132 with mechanical fasteners, such as threaded screws or studs, latches or others. In one embodiment, threaded studs 136 may extend through drilled and tapped holes in the wall of the hollow cylinder 132, the holes extending from a first end to a second end of the hollow cylinder 132. The threaded studs 136 may extend through the drilled and tapped holes in the wall to engage drilled and tapped holes in an upper surface 137 of the bottom disk 134, while any type of threaded nut 139 (e.g., a wing nut) may be threaded onto an upper end of the threaded stud 136. In this manner, the bottom disk 134 may be attached to the bottommost end of the hollow cylinder 132, and no fasteners are present which protrude from the bottom surface 135 of the bottom disk 134.

In one embodiment, the depth of the first reservoir 110 is less than three times a diameter of the bottom surface 135 of the bottom disk 134 of the second reservoir 130. In another embodiment, the depth of the first reservoir 110 is less than two times a diameter of the bottom surface 135 of the bottom disk 134 of the second reservoir 130. Further, in one embodiment, the diameter of the first reservoir 110 is less than two times a diameter of the bottom surface 135 of the bottom disk 134 of the second reservoir 130. In another embodiment, the diameter of the first reservoir 110 may be less than 1.5 times a diameter of the bottom surface 135 of the bottom disk 134 of the second reservoir 130.

In one embodiment, the second reservoir 130 further includes a circumferential flange 106 disposed at or near an upper end of the hollow cylinder 132. The flange 106 may be a separate component attached to the hollow cylinder 132, or formed integrally with the hollow cylinder 132. The flange 106 may rest on a plurality of bearings 104 which allow free rotation of the second reservoir 130, and in turn, rotation of the bottom disk 134. The plurality of bearings 104 may be coupled or attached to a fixed structure, such as a stand or other structure strong enough to fully support the second reservoir 130. As shown, the fixed structure may include two or more vertical members 102 having a larger base portion. A horizontal member 103 is attached between the two or more vertical members 102, and the plurality of bearings 104 may be coupled to the horizontal member 103. As shown, the flange 106 of the second reservoir 130 rests on the plurality of bearings 104 so that the second reservoir 130 is suspended above and extends into the first reservoir 110. The horizontal member 103 of the fixed structure may be adjustable along lengths of the vertical members 102 so that a height of the suspended second reservoir 130 may be adjusted. Changing a height of the suspended second reservoir 130 adjusts the extent to which the bottom surface 135 is submerged in the first fluid 112 in the first reservoir 110.

In one embodiment, the testing apparatus 100 further includes a coolant fixture 120 that extends into the second reservoir 130 and remains fixed while the second reservoir 130 rotates around central axis A. The coolant fixture 120 includes a fluid inlet 122 for delivering the second fluid 138 to the second reservoir 130, and a fluid outlet 124 for removing or taking away the second fluid 138 from the second reservoir 130. For example, the fluid inlet 122 and fluid outlet 124 may be attached to a fluid storage tank (not shown) from which the second fluid is provided. The fluid inlet 122 may be coupled with a cylindrical thin-walled tube 129 arranged in a substantially vertical orientation and extending into the second reservoir 130. The cylindrical tube 129 may extend into the second reservoir 130 toward the bottom disk 134, but not contact the bottom disk 134. An outer cylindrical housing 128, having a larger diameter than that of the cylindrical tube 129, may be concentrically disposed about the cylindrical tube 129, thereby forming an annulus 126 between the cylindrical tube 129 and the outer housing 128. The outer housing 128 may include an aperture 123 in an outer wall thereof and located near an upper end of the outer housing 128 where the fluid outlet 124 is coupled. Coolant fluid may enter the second reservoir 130 through the fluid inlet 122 and cylindrical tube 129. Coolant fluid may exit the second reservoir 130 through the annulus 126 and fluid outlet 124. Alternatively, although not shown, coolant fluid may enter the second reservoir 130 through a fluid inlet connected with the annulus 126, and exit the second reservoir 130 through the cylindrical tube 129. A pump (not shown) may be used to circulate fluid into the second reservoir 130 through the fluid inlet 122 and out the fluid outlet 124.

Figure 2:
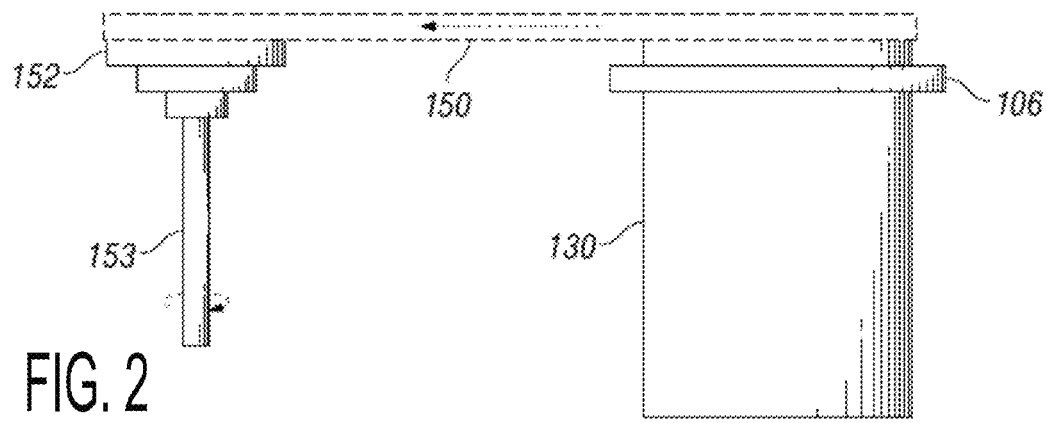
FIG. 2 illustrates a side view of the second reservoir shown in FIG. 1.
Figure 3:
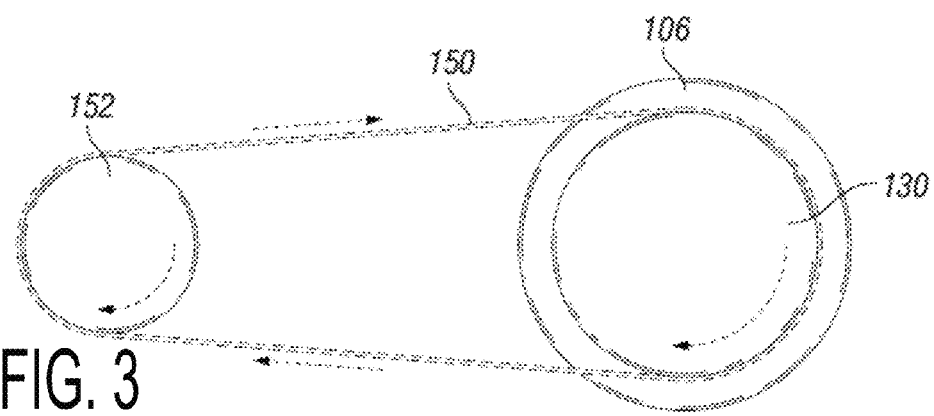
FIG. 3 illustrates a top view of FIG. 2.

As previously described, the second reservoir 130 is rotatable about central axis A. As shown in FIGS. 2 and 3, a belt 150 is used to couple the second reservoir 130 with a rotating shaft 153 of a motor (e.g., a motor belt system which is not shown). The motor is mounted separately from the fixed structure (e.g., vertical members 102 and horizontal member 103) and first and second reservoirs 110 and 130 to eliminate any vibration contribution to the flow field in the first reservoir. The belt 150 may be coupled to or extend around all or a portion of the second reservoir 130 at a location proximate to the flange 106, at an upper portion of the second reservoir 130. Alternatively, the belt 150 may be coupled to or extend around a portion of the second reservoir 130 at any suitable location for rotating the second reservoir 130. The belt 150 also is coupled with and extends around a gear wheel 152 attached at an end of a motor shaft 153. Gear wheels 152 having different diameters may be used in conjunction with rotating the second reservoir 130 to change a rotation speed of the second reservoir 130 given a constant torque or power output by the motor. The rotation speed in can be adjusted to test laminar and turbulent flow during deposition. Further, the belt 150 may be a material having a certain amount of elasticity (e.g., rubber), which aids in dampening any vibrations produced by rotating the second reservoir.

Figure 4:
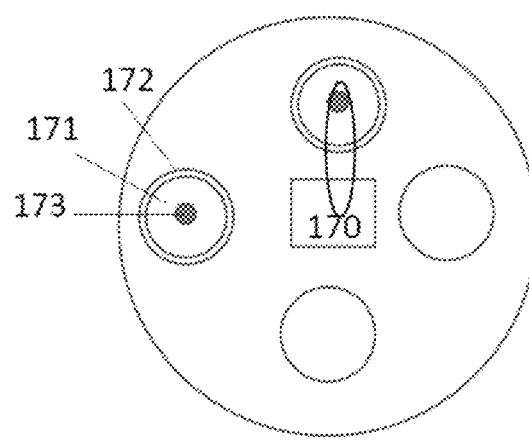
FIG. 4 illustrates a top view of a test apparatus assembly with multiple reservoirs for testing.

FIG. 4 illustrates a top view of a test apparatus assembly with multiple reservoirs for testing different fluids, inhibitors, or under different conditions of laminar and turbulent flows. The assembly is operated with a single motor 170 allowing identical speed for all of the reservoirs. Each reservoir 172 is provided with a rotating cold disk 173 for the testing of the same or different test fluids 171.

The claimed subject matter is not to be limited in scope by the specific embodiments described herein. Indeed, various modifications of one or more embodiments disclosed herein in addition to those described herein will become apparent to those skilled in the art from the foregoing descriptions. Such modifications are intended to fall within the scope of the appended claims.

As used in this specification and the following claims, the terms "comprise" (as well as forms, derivatives, or variations thereof, such as "comprising" and "comprises") and "include" (as well as forms, derivatives, or variations thereof, such as "including" and "includes") are inclusive (i.e., open-ended) and do not exclude additional elements or steps. Accordingly, these terms are intended to not only cover the recited element(s) or step(s), but may also include other elements or steps not expressly recited. Furthermore, as used herein, the use of the terms "a" or "an" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%.

What is claimed:
1. A testing apparatus for qualifying a composition for use to reduce scale deposition, the apparatus comprising:
    a first reservoir capable of holding a first fluid containing chemical inhibitors to be tested;
    a second reservoir having an approximately flat bottom plate having an upper surface and a bottom surface, the second reservoir is disposed within the first reservoir, the second reservoir capable of holding a second fluid;

wherein the second reservoir is configured for the approximately flat bottom plate to be at least partially submerged in the first fluid for the first fluid to be in contact with the bottom surface so that a scale deposition from the first fluid is deposited onto the bottom surface of the approximately flat bottom plate;

wherein the second reservoir is configured for the approximately flat bottom plate to be rotatable at variable speeds imparting shear stresses onto the first fluid in contact with the bottom surface.

2. The apparatus of claim 1, wherein the second reservoir is a hollow body arranged in an approximately vertical manner and rotatable about a vertical central axis; and wherein the approximately flat bottom plate is attached at a bottommost end of the hollow body.

3. The apparatus of claim 2, further comprising one or more mechanical fasteners for attaching the approximately flat bottom plate to the bottommost end of the hollow body.

4. The apparatus of claim 3, further comprising a sealing mechanism disposed between the hollow body and the approximately flat bottom plate.

5. The testing apparatus of claim 1, wherein a height of the first reservoir is less than three times a width of the second reservoir, and wherein a width of the first reservoir is less than two times a width of the second reservoir.

6. The testing apparatus of claim 1, wherein the composition to qualify is a chemical inhibitor and the scale deposition is a wax deposition.

7. The testing apparatus of claim 6, wherein the second reservoir contains a heat transfer fluid selected from water and coolants, and the first reservoir contains a crude oil for evaluating wax deposition in the crude oil.

8. The testing apparatus of claim 1, further comprising:
a first temperature control device for adjusting a temperature of the first fluid to at or above a temperature $T_1$; and
a second temperature control device for adjusting a temperature of the second fluid to at or below a temperature $T_2$.

9. The testing apparatus of claim 8, wherein temperature $T_2$ is less than temperature $T_1$.

10. The testing apparatus of claim 8, wherein temperature $T_2$ is less than a Wax Appearance Temperature of the first fluid.

11. The apparatus of claim 1, further comprising
a fluid inlet through which the second fluid enters the second reservoir, and a fluid outlet through which the second fluid exits the second reservoir.

12. The apparatus of claim 11, further comprising:
a cooling fixture coupled with the fluid inlet and fluid outlet, the cooling fixture comprising:
a cylindrical tube coupled with the fluid inlet and extending into the second reservoir; and
an outer housing coupled with the fluid outlet and concentrically disposed over the cylindrical tube,
wherein an annulus is formed between diameters of the cylindrical tube and the outer housing.

13. The apparatus of claim 12, wherein fluid enters the second reservoir through the cylindrical tube and exits the second reservoir through the annulus.

14. The apparatus of claim 12, wherein the first fluid is crude oil and the second fluid is a heat transfer fluid.

15. The apparatus of claim 1, wherein the second reservoir comprises a flange which rests on a plurality of bearings allowing the second reservoir to rotate;

wherein the second reservoir is configured for the approximately flat bottom plate to be at least partially submerged in the first fluid for the first fluid to be in contact with the bottom surface so that a scale deposition from the first fluid is deposited onto the bottom surface of the approximately flat bottom plate;

wherein the second reservoir is configured for the approximately flat bottom plate to be rotatable at variable speeds imparting shear stresses onto the first fluid in contact with the bottom surface.

16. A method for qualifying a composition used to reduce scale deposition, the method comprising:
providing a first reservoir capable of holding a first fluid, and a second reservoir capable of holding a second fluid, the second reservoir having an approximately flat bottom plate with an upper surface and a bottom surface;
filling the first reservoir with a first fluid having a temperature $T_1$, the first fluid containing a composition to be qualified;
filling the second reservoir with a heat transfer fluid having a temperature $T_2$;
contacting the bottom surface of the approximately flat bottom plate with the first fluid in the first reservoir;
causing the approximately flat bottom plate to rotate at a given speed;
maintaining the temperatures such that $T_2$ is less than $T_1$; and
collecting a scale deposition from the first fluid deposited on the bottom surface of the approximately flat bottom plate.

17. The method of claim 16, further comprising imparting variable shear stresses on the first fluid at varying radial locations of the bottom surface of the second reservoir.

18. The method of claim 16, further comprising maintain a uniform temperature at varying radial locations of the bottom surface of the second reservoir.

19. The method of claim 16, further comprising adjusting the temperature $T_2$ of the second fluid to be less than a Wax Appearance Temperature of the first fluid.

20. The method of claim 16, wherein the flat bottom plate is rotated at sufficient speed to simulate turbulent flow in the first fluid in contact with the bottom surface.

21. A method for simulating flow conditions in evaluating compositions used to reduce scale deposition, the method comprising:
providing a first reservoir capable of holding a first fluid, and a second reservoir capable of holding a second fluid, the second reservoir having an approximately flat bottom plate with an upper surface and a bottom surface;
filling the first reservoir with a first fluid having a temperature $T_1$, the first fluid containing a composition to be qualified;
filling the second reservoir with a heat transfer fluid having a temperature $T_2$;
contacting the bottom surface of the approximately flat bottom plate with the first fluid in the first reservoir;
maintaining the temperatures such that $T_2$ is less than $T_1$; and
causing the approximately flat bottom plate to rotate at a sufficient speed to simulate any of laminar or turbulent flow field giving rheological properties of the first fluid and dimensions of the first and second reservoirs.

* * * * *